United States Patent [19]

Babaian

[11] Patent Number: 5,624,263

[45] Date of Patent: Apr. 29, 1997

[54] DENTAL FOIL COMPRESSION DEVICE

[76] Inventor: Armen A. Babaian, 9345 Belvoir Ave., La Crescenta, Calif. 91214

[21] Appl. No.: 583,779

[22] Filed: Jan. 11, 1996

[51] Int. Cl.[6] .............................. A61C 5/10; A61C 5/08; A61C 13/00

[52] U.S. Cl. .................... 433/223; 433/227; 433/218

[58] Field of Search ........................... 433/227, 223, 433/218; 72/467, 343, 354.2, 355.2, 360

[56] References Cited

U.S. PATENT DOCUMENTS

| | | | |
|---|---|---|---|
| 2,751,676 | 6/1956 | Kaul | 72/355.2 |
| 4,050,283 | 9/1977 | Schober | 72/360 X |
| 5,014,532 | 5/1991 | Shoher et al. | 433/223 X |
| 5,073,113 | 12/1991 | Hornig | 433/223 |
| 5,314,335 | 5/1994 | Fung | 433/223 |
| 5,445,770 | 8/1995 | Adam et al. | 433/223 X |

*Primary Examiner*—Nicholas D. Lucchesi
*Attorney, Agent, or Firm*—Gene Scott - Patent Law & Venture Group

[57] ABSTRACT

A dental foil compressing apparatus is constructed of two parts which engage to form a closed cavity. A viscous material is placed into the cavity so that engagement of the two parts causes a hydrostatic compressive force within the cavity to compress a foil against a dental model supported within the cavity. The dental model is placed near the parting line of the engagement of the two parts so as to be easily loaded and unloaded.

5 Claims, 3 Drawing Sheets

DENTAL FOIL COMPRESSION DEVICE

BACKGROUND OF THE INVENTION

1. Field of the Invention

This invention relates generally to compression tools, and more particularly to an improved dental compression apparatus for generating compression in the dental porcelain laminate foil technique.

2. Description of Related Art

Invention and use of dental foil compression devices is known in the medical arts such as the porcelain laminate foil technique. FIG. 4 shows a cross-sectional view of a well known, prior art tool for achieving compression of foils against dental models known as dies. Generally, the problem is how to compress a thin metallic foil against a plaster model of a tooth or other dental structure so that the foil is able to be impressed with the surface contour and roughness of the dental structure. In a later step in the process, the foil will be used as a base for building up a thin porcelain cap or other structure to be fitted over a tooth of a patient. Therefore, the foil must be energetically impressed on the model so as to capture its surface contour with fidelity. The apparatus shown in FIG. 4 is used to achieve such a result. A base portion 50 is a cylindrical fixture having a cavity machined within it. Inside the cavity is placed a dental model holder 30 with the model 60 within it. This is placed over a washer 40 at the bottom of the cavity. A viscous material such as a clay 20 is pressed into the cavity over the dental model 60. A pin 240 extending from the model 60 is used to position the model 60 at the center of the fixture, the pin being positioned within a hole 90 in the washer 40. Further viscous material 20 is pressed into a small cavity in a ram rod 10. The ram rod 10 is then forced into the base portion 50 driving the viscous material 20 into compression and thereby driving the foil against the tooth of the model 60. One major problem with this approach is that the ram rod 10, because it enters the base portion, often damages the model 60. Another problem with this prior art approach is that when the ram rod 10 is removed from the base portion 50, it is not possible to easily remove the model 60. In order to facilitate its removal, a push rod 70 is usually provided. This rod 70 fits within a small diameter hole 80 in the base portion 50 and is able to push against the washer 40, dental model holder 30, model 60 and viscous material 20 to try to dislodge this entire group of items together. However, the washer 40 often tends to bind within the base portion 50 so that it is difficult to remove the model 60. Even when the group is dislodged from the base portion 50, it is not easy to remove the model, in that when the washer 40 has been separated from the dental model holder 30, the model is not easily grasped since it is embedded in the viscous material and is held tightly inside the holder 30. The sharp pin 240 (see FIG. 3) makes this approach to removal of the model even more difficult and problematic. There is a need for a more suitable fixture for accomplishing the same result as the prior art device of FIG. 4 but which is less complex, less expensive to fabricate, and which is easier to load and unload.

The present invention fulfills these needs and provides further related advantages as described in the following summary.

SUMMARY OF THE INVENTION

The present invention is an improved apparatus and method for compressing a foil against a dental model. It has been found that by placing a significant amount of the viscous material both above as well as below the model, and by joining the fixtures roughly at the position which the model takes within the cavity, the disadvantages of the prior art device are overcome. The invention includes a first and a second fixtures which engage, one within the other, but the fixture holding the model is not entered by the opposing fixture. The apparatus includes only these two parts instead of the five parts necessary for the prior art device. The constructional details of the two parts make the device simple and inexpensive to fabricate, being made by simple lathe cutting operations. The constructional details also make for a device which is much easier to use. With the first of the two fixtures nearly filled with the viscous material, and with the model place on top of the material so that the model is in the mouth of the first fixture, viscous material within the second of the two fixtures is able to be brought over the dental model, thereby compressing the foil. When the second of the two fixtures is removed from the first, the model is easily grasped for removal from the first fixture.

Thus it is an object of the present invention to provide an improved dental foil compressing apparatus. It is a further object to provide such an apparatus having only two easily fabricated parts. It is a further object of the present invention to provide such an apparatus that has the advantage of being easy to load and remove the workpiece, i.e., the dental model. It is a final object of the present invention to provide a method of use of the apparatus that is easier then that taught in the prior art.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention, a device for compressing a foil onto a dental model. In such drawings.

DETAILED DESCRIPTION OF THE PREFERRED EMBODIMENT

Figure 1:
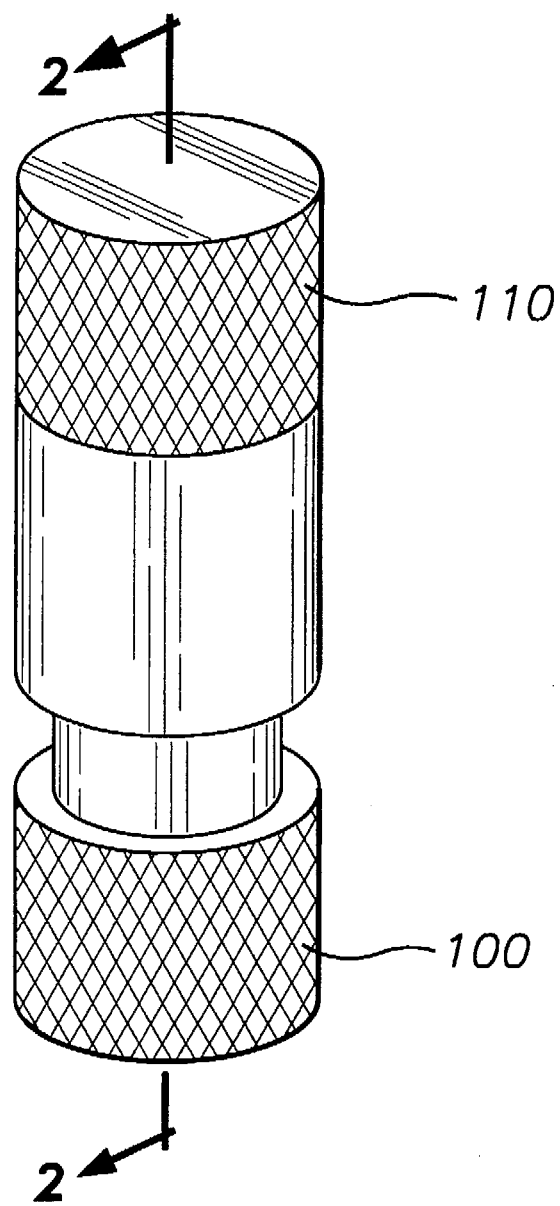
FIG. 1 is a perspective view of the preferred embodiment of the present invention, particularly showing a pair of engagable fixtures.
Figure 2:
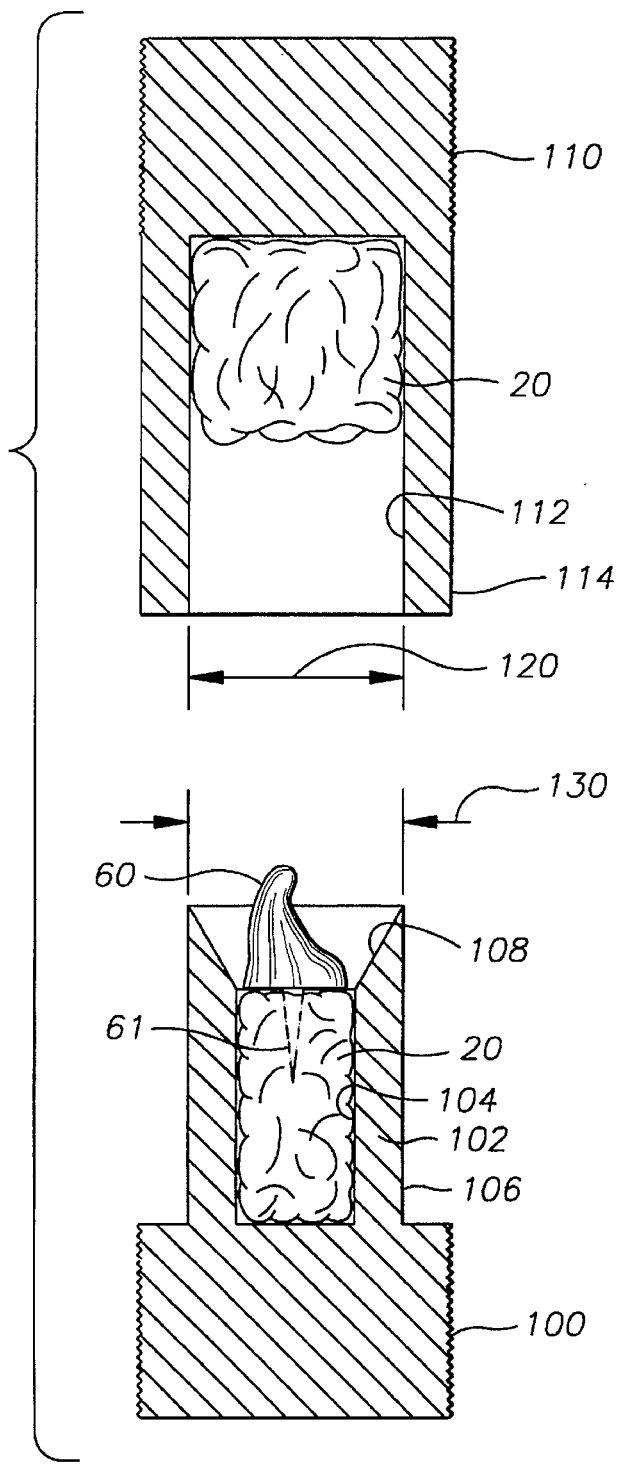
FIG. 2 is an exploded front elevational cross-sectional view thereof, taken along line 2—2 of FIG. 1, and particularly showing the interior of the fixtures and the placement of a dental model and a viscous incompressible material therein.
Figure 3:
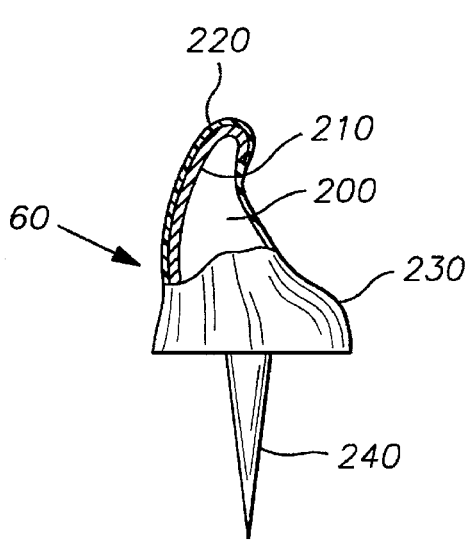
FIG. 3 is an partial breakaway view as an enlargement of the dental model shown in FIG. 2.
Figure 4:
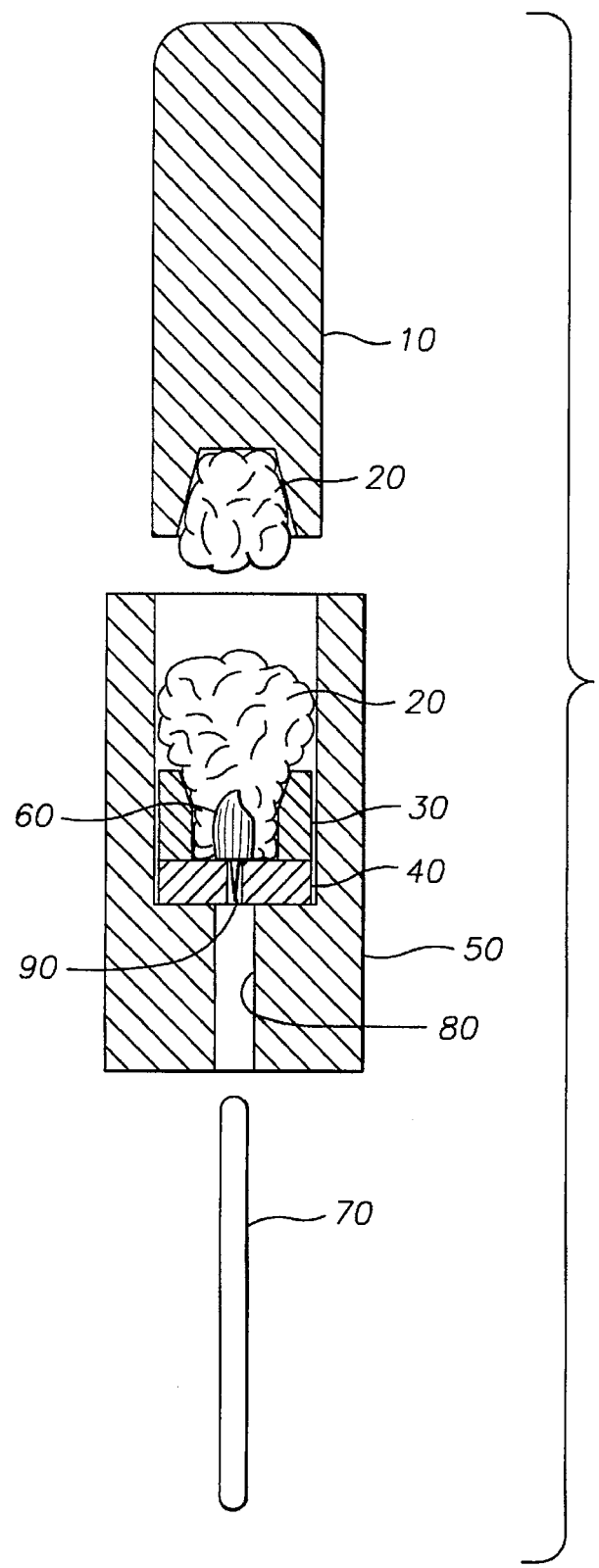
FIG. 4 is an exploded front elevational cross-sectional view of a prior art device showing interior details thereof.

The above described drawing figures illustrate a device for compressing a foil 210 against a dental model 60. The apparatus includes a first cylindrical walled fixture 100 defining a first cavity 100C with a conically shaped mouth 108. The apparatus further includes a second cylindrical walled fixture 110 defining a second cavity 110C. The two fixtures 100,110 are mutually engagable, the first fixture 100 sliding within the second fixture 110 with the outer surface 106 of the first fixture 100 moving past the inner surface 112 of the second fixture 110. When these fixtures are engaged, a viscous material 20 of a type and consistency well known in the dental arts, which is pressed within the cavities, is compressed. The dimensional tolerance between these two surfaces must be such as to allow air to escape from the cavities when the fixtures are engaging, but to not allow the viscous material to escape. It has been found, through experimentation, that the outside diameter 130 of the first fixture must not differ from the inside diameter 120 of the second fixture, by more than 0.005 inches and by less then 0.001 inches. If the viscous material is able to escape from the fixtures, then the ultimate compressive force is not delivered to the foil. This structural imperative is, therefore, the key to the successful operation of the device. With the fixtures 100, 110 fully engaged, the volume of the first and second cavities 100C, 110C is approximately equal to the volume of the first cavity 100C alone, i.e., the first fixture 100 fills the second cavity 110C. The first cavity 100C, except for the conically shaped mouth 108, is filled with the viscous incompressible material 20 which is a well known dental clay. The foiled dental model 60 is held on, and supported by, a surface 21 of the viscous material 20 in the first fixture 100. In this position the dental model 60 is approximately enclosed within the mouth 108 of the first cavity 100. It is important that this mouth be conically shaped and have an acceptance angle of approximately 90 degrees. The second cavity also is filled with some of the viscous material 20, but only the distal, approximately one-half of the second cavity 110C is so filled. When the fixtures 100, 110 are forced energetically into mutual engagement, the force of engagement compacts the viscous material 20 within the cavities 100C and 110C causing the foil 210 to compress against a model tooth 200 of the dental model 60. The conical shape and angle of the mouth of the first fixture 100 causes the viscous material to flow against the model 660 but cannot damage it. In order for the apparatus to achieve its objective it is preferably made of a rigid structural material such as steel. However any rigid structural material able to withstand the force of compression of the viscous material and which may be formed with close tolerances, may be used.

In operation the invention method results in compressing the foil 210 onto the face of the tooth 200 of the dental model 60. The fixtures 100, 110 are filled to the appropriate level with the viscous material 20. The tooth 200 is covered with the foil 210; usually a foil of a precious metal is used because such metallic foils can be made as a relatively thin sheet, providing an advantage in fine surface contour reproduction. The tooth 200 and foil 210 are then covered with a plastic film sheet 220 as an outer protective coating. The fixtures 100, 110 are then coupled and forced energetically into full mutual engagement so that the force of engagement compacts the viscous material within the cavities and importantly, against, and all around, the model 60. The fixtures are then separated by pulling them apart. The dental model 60 is easily reached and removed manually from the first fixture 100. The sharp pin 240 is not directed toward the mouth of the fixture 100.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A method for compressing a foil onto the face of a dental model, the method comprising the steps of:

a) providing a first cylindrical walled fixture defining a first cavity with a conically shaped mouth;

b) providing a second cylindrical walled fixture defining a second cavity, the volume of the cavities being approximately equal to the volume of the first cavity when the fixtures are mutually engaged;

c) filling the first cavity, except the conically shaped mouth, with a viscous incompressible material;

d) placing a foiled dental model on the viscous material in the first fixture, in a position wherein the dental model is approximately enclosed within the mouth of the first cavity;

e) filling the distal, approximate one-half, of the second cavity with the viscous material;

f) forcing the fixtures energetically into mutual engagement so that the force of engagement compacts the viscous material within the cavities generating a hydrostatic compressive force within the cavities compressing the foiled dental model;

g) separating the fixtures to obtain access to the dental model.

2. An apparatus for compressing a foil onto the face of a dental model, the apparatus comprising:

a first cylindrical walled fixture defining a first cavity with a conically shaped mouth;

a second cylindrical walled fixture defining a second cavity, the volume of the first and second cavities being approximately equal to the volume of the first cavity when the fixtures are mutually engaged;

the first cavity, except the conically shaped mouth, filled with a viscous incompressible material;

a foiled dental model held on a surface of the viscous material in the first fixture, the dental model being approximately enclosed within the mouth of the first cavity;

a distal, approximately one-half of the second cavity filled with the viscous material;

whereby by forcing the fixtures energetically into mutual engagement so that the force of engagement compacts the viscous material within the cavities, the foil is compressed against the dental model.

3. An apparatus for compressing a foil onto the face of a dental model, the apparatus comprising:

a dental model of a tooth;

a foil in contact with the model;

a first cylindrical walled fixture defining a first cavity with a conically shaped mouth;

a second cylindrical walled fixture defining a second cavity, the volume of the first and second cavities being approximately equal to the volume of the first cavity when the fixtures are mutually engaged;

the first cavity, except the conically shaped mouth, filled with a viscous incompressible material;

the dental model, with the foil, held on a surface of the viscous material in the first fixture, the dental model being approximately enclosed within the mouth of the first cavity;

a distal, approximately one-half of the second cavity filled with the viscous material;

whereby by forcing the fixtures energetically into mutual engagement so that the force of engagement compacts the viscous material within the cavities, the foil is compressed against the dental model.

4. The apparatus of claim 3 wherein the fixtures are cylinders of a rigid structural material, an outer diameter of the first fixture being a sliding fit within the second cavity.

5. The apparatus of claim 3 wherein the conically shaped mouth has an acceptance angle of approximately 90 degrees.

* * * * *